US011123281B2

(12) United States Patent
Russell

(10) Patent No.: US 11,123,281 B2
(45) Date of Patent: Sep. 21, 2021

(54) OXYDATION DYE DELIVERY PRODUCT OR PROCESS

(71) Applicant: PWAI, LLC, Salem, MA (US)

(72) Inventor: Marsha A. Russell, Beverly, MA (US)

(73) Assignee: PWAI, LLC, Salem, MA (US)

( * ) Notice: Subject to any disclaimer, the term of this patent is extended or adjusted under 35 U.S.C. 154(b) by 0 days.

(21) Appl. No.: 16/660,729

(22) Filed: Oct. 22, 2019

(65) Prior Publication Data

US 2020/0121583 A1 Apr. 23, 2020

Related U.S. Application Data

(60) Provisional application No. 62/748,770, filed on Oct. 22, 2018.

(51) Int. Cl.
*A61Q 5/10* (2006.01)
*A61K 8/73* (2006.01)
*A61K 8/02* (2006.01)

(52) U.S. Cl.
CPC .............. *A61K 8/73* (2013.01); *A61K 8/022* (2013.01); *A61Q 5/10* (2013.01); *A61K 2800/4322* (2013.01); *A61K 2800/4324* (2013.01); *A61K 2800/882* (2013.01)

(58) Field of Classification Search
CPC .............. A61Q 5/10; A61K 2800/882; A61K 2800/4322; A61K 8/73; A61K 8/4324; A61K 8/022
USPC .............................................. 8/405; 132/208
See application file for complete search history.

(56) References Cited

U.S. PATENT DOCUMENTS

| 9,283,158 B2 * | 3/2016 | Goutsis ................... A61K 8/73 |
| 2005/0000035 A1 | 1/2005 | Chan et al. |
| 2005/0102770 A1 | 5/2005 | Kiyonmine et al. |
| 2005/0193501 A1 | 9/2005 | Chan et al. |
| 2006/0075580 A1 | 4/2006 | Chan et al. |
| 2010/0154140 A1 | 6/2010 | Simonet et al. |

OTHER PUBLICATIONS

International Search Report dated May 7, 2020 from corresponding PCT/US19/57495, pp. 1-5.
International Written Opinion dated May 7, 2020 from corresponding PCT/US19/57495, pp. 1-6.
Rastogi et al. Precursors of Oxidative Hair Dyes in Hair Colouring Formulations. Jan. 2003 [Retrieved Feb. 28, 2020] Retrieved from Internet URL: < https:/lwww2.dmu.dk/1_viden/2_Publikationer/3_arbrapporter/rapporter/AR175.pdf >.

* cited by examiner

*Primary Examiner* — Eisa B Elhilo
(74) *Attorney, Agent, or Firm* — Law Offices of Daniel A. Tesler, LLC

(57) ABSTRACT

Disclosed in this application is a hair coloring additive and method of use that provides highly accurate and long-lasting hair coloring results. In some aspects, the hair coloring additive uses raw oxidation dye molecules that are sized to enter into the cortex of the hair during the method of application, where they grow and remain trapped. The hair coloring additive and methods of use can be used with multiple types of hair coloring donor products or formulas, including temporary, semi-permanent, demi-permanent and permanent hair colors.

20 Claims, 1 Drawing Sheet

| Grey Level Scale | Percent Grey | No Grey Level Scale | % Grey | | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|
| | | | 100 | 75 | 50 | 0 | 100 | 75 | 50 | 0 | 100 | 75 | 50 | 0 | 100 | 75 | 50 | 0 | 100 | 75 | 50 | 0 | 100 | 75 | 50 | 0 | 100 | 75 | 50 | 0 | 100 | 75 | 50 | 0 | 100 | 75 | 50 | 0 | 100 | 75 | 50 | 0 |
| 10 | 100% | 10 | # Additive Packs | | | | | | | | | | | | | | | | | | | | | | | | | | | | | | | | | | | | | | |
| 9 | 75% | 9 | 3 | 2 | 1 | | 3 | 2 | 1 | | 3 | 2 | 1 | | 3 | 2 | 1 | | 3 | 2 | 1 | | 3 | 2 | 1 | | 3 | 2 | 1 | | 3 | 2 | 1 | | 3 | 2 | 1 | | 3 | 2 | 1 | |
| 8 | 50% | 8 | 3 | 2 | 1 | | 3 | 2 | 1 | | 3 | 2 | 1 | | 3 | 2 | 1 | | 3 | 2 | 1 | | | | | | | | | | | | | | | | | | | | | |
| 7 | | 7 | # Additive Packs | | | | | | | | | | | | | | | | | | | | | | | | | | | | | | | | | | | | | | |
| 6 | 50% | 6 | 3 | 2 | 1 | | 3 | 2 | 1 | | 3 | 2 | 1 | | | | | | | | | | | | | | | | | | | | | | | | | | | | | |
| 5 | | 5 | 3 | 2 | 1 | | 3 | 2 | 1 | | | | | | | | | | | | | | | | | | | | | | | | | | | | | | | | | |
| 4 | | 4 | 3 | 2 | 1 | | | | | | | | | | | | | | | | | | | | | | | | | | | | | | | | | | | | | |
| 3 | | 3 | # Additive Packs | | | | | | | | | | | | | | | | | | | | | | | | | | | | | | | | | | | | | | |
| 2 | | 2 | # Additive Packs | | | | | | | | | | | | | | | | | | | | | | | | | | | | | | | | | | | | | | |
| 1 | | 1 | # Additive Packs | | | | | | | | | | | | | | | | | | | | | | | | | | | | | | | | | | | | | | |

OXYDATION DYE DELIVERY PRODUCT OR PROCESS

CROSS REFERENCE TO RELATED APPLICATIONS

This application claims the benefit of U.S. Provisional Patent Application No. 62/748,770 filed Oct. 22, 2018, which is hereby incorporated by reference in its entirety.

FIELD

The present disclosure relates to hair coloring, specifically to a hair coloring additive that enhances, alters or modifies the effectiveness and color accuracy of other hair coloring products.

BACKGROUND

Humans have colored their hair for thousands of years and the first known pictures date back to the Cleopatra era in Egyptian History. In these times hair dyes were derived from plants and minerals and needed to be applied often due to the fact they attached to the outside of the hair shaft thus making them easy to remove. Simple washing of the hair, combing, submitting it to sunlight or even touching the hair would diminish the bond of the hair dyes on the hair shaft.

BRIEF SUMMARY

During the 1860's a major breakthrough was discovered in the field of hair coloring. The introduction of hair dyes manufactured from by-products such as coal tar were chosen and considered the key component of the first known synthetic chemical hair dyes. Over the following fifty years, chemists diligently worked on creating ways to enhance these hair dyes and properly secure them to the hair shaft. In 1907, the first commercial hair dye products were introduced. Although these early products could color hair, they did not last very long once applied.

Even though many years have passed, the modern hair coloring industry still relies on technology that's over 100-years old. Synthetic hair dyes produced from petroleum-based coal tars are considered a health risk as they contain dye intermediates such as Paraphenylenediamine (hereinafter, "PPD"). Many attempts have been made to revert back to the technology and ingredients used before the 1860's due to health and safety concerns. Although the toxic levels of PPD in modern hair dyes are much lower than in early commercial hair dye products, the levels of PPD in modern hair dyes are still considered unhealthy and can produce allergic reactions in a small percentage of clients having their hair colored. The industry recommends testing clients regularly for allergic reactions to PPD prior to hair coloring. PPD is most harmful to the person who applies the hair color as part of their daily job such as hairdressers due to the long-term exposure to the chemical.

As the world focuses more on organic and natural alternatives to hair dyes that contain PPD, manufacturers have struggled to produce hair dyes that are both safe and effective. Currently, over 95% of all hair dyes manufactured contain PPD. When entering a hair salon, generally over 99% of the hair dyes contain PPD because of their superior properties and end results. Box hair dyes, also referred to as home hair coloring kits, are the hair dyes that are most likely to be formulated without PPD. Box hair dyes primarily cater to the home-based customer rather than the professional and the smaller group of "Green" clients willing to swap effectiveness for health and safety.

Human Hair Structure

Human hair is a complex structure composed of 45.2% Carbon, 27.9% Oxygen, 6.6% Hydrogen, 15.1% Nitrogen and 5.2% Sulphur. Four physical regions make up the structure of hair: the mantle, cuticle, cortex and medulla. The cuticle is the outside layer of hair, which is a scale-like armored covering that protects the inside proteins of hair from the outside elements. Within the cuticle layer is an interwoven body of keratin cells known as the cortex. The cortex is recognized for adding the strength to hair and it's the carrier of melanin, a pigmented solution responsible for determining the color of hair. At the center of the cortex is an air void known as the medulla. The medulla is an open reservoir that can be used for water, oil, air or dye absorbed during the hair color altering process of the hair's physical structure. The mantle is a protective fluid layer that covers the outside of the cuticle. The mantle comprises oil, salt and water. The primary propose of the mantle is to maintain the proper potential hydrogen level (hereinafter, "pH") on the outside of the hair shaft. The proper pH of the mantle is generally about 4.5-5.0.

By nature, hair is very strong and contains a large percentage of oxidative elements. The keratin cells within the cortex comprise 18-amino acids that form elongated cells that are then linked together in a polypeptide chain, a chain-like structure. The attachment points of the polypeptide chain are referred to as peptide bonds or end bonds. There are three types of peptide bonds: hydrogen, salt and disulfide bonds. Hydrogen bonds make up the majority of peptide bonds in hair and are relatively weak bonds that can be broken by water and reattached by drying the hair. Salt bonds are also weak bonds that require alkaline or increases in pH to break the bond. Disulfide bonds are atomic bonds that are the strongest and provide the most of hair's strength. Disulfide bonds are broken only by altering the atomic structure of the hair.

Human hair is generally at its maximum shine and strength when it is at a pH level of about 4.5-5.0. At this pH level, the cuticle scales are closed, making the hair shaft smooth to the touch. Simply washing your hair and removing the mantle can change the hair's pH resulting in an immediate change in look and feel. After washing, the mantle must be regenerated by the body naturally or by applying conditioning solutions. In many instances, unwashed hair can be the shiniest and strongest due to the presence of a strong mantle.

Categories of Hair Coloring Products and Processes

There are various options available when deciding whether to color hair. Hair coloring processes can be broken down into four categories: temporary, semi-permanent, demi-permanent and permanent. The hair dyes used in these processes are direct dyes, basic dyes, cationic basic dyes and oxidation dyes. As the quality of hair coloring services increase additional chemicals can be introduced to the process that work as a catalyst for the hair dying process. The additional chemicals can be classified into two groups: alkali and oxidizers.

A primary purpose of an alkali can be to soften, swell and open the cuticle so that the other coloring ingredients can penetrate the hair shaft. A secondary purpose of an alkali can be to manipulate the salt bonds within the hair shaft. Alkalis work by altering the pH level in and on the hair. There are various alkalis used in in hair coloring processes, but the most common alkali used is Ammonium Hydroxide (hereinafter, "ammonia").

A primary purpose of an oxidizer can be to soften the cortex and expose the melanin inside the hair shaft. A secondary purpose of an oxidizer can be to relax the bonds within the polypeptide chain so that the hair shaft can be manipulated and allowed to accept the deposit or removal of hair dyes. The terms "lift" and "deposit" are used to signify the amount of melanin or hair dye removed or added to the cortex. The term "lift," as used herein, refers to the removal of melanin or hair dye from any portion of the hair shaft. The term "deposit," as used herein, refers to the addition of melanin or hair dye to any portion of the hair shaft. Generally, more lift is achieved when more oxidizer is used, resulting in the lightening of the hair color. Generally, less lift is achieved when less oxidizer is used, resulting in darker hair colors. An appropriate oxidizer for the hair coloring process is hydrogen peroxide ($H_2O_2$).

Hair Dyes can be combined with heat, an alkali and an oxidizer to create an oxidizing solution capable of producing extensive results. Because hair is made of several oxidative groups, oxidizers hold the ability to drastically change the physical structure of the hair shaft. The permanent hair coloring process can work by damaging the hair, altering its structure and then repairing the damage. The pH level of the hair is an important factor to understand when coloring hair. The higher the pH, the more open the cuticle and the lower the pH, the more closed the cuticle. There are various approaches to hair coloring in the marketplace.

Temporary Hair Color

Temporary hair colors are solutions that are formulated to produce temporary results that last for 2-3 hair washes. Examples of temporary hair coloring products are dye pigmented shampoos, dye pigmented rinses and temporary hair colors. Temporary hair coloring products do not use an alkali or oxidizer and rely only on the deposit of direct or basic dyes with large molecular structures. The large dye molecules can't penetrate the cuticle and remain on the outside of the hair shaft, making them easy to remove. Electrical charges can be used to attach the basic dyes onto the hair shaft's surface. Temporary products are usually only offered in the most aggressive dye shades that make them the brightest and boldest of all hair colors. Temporary hair colors are most commonly used by the person attempting to make a personal statement or the user trying to mask grey hair. Pigmented shampoos and rinses are often considered maintenance tools used for maintaining an existing hair color. It is very important that hair is not damaged prior the application of temporary hair colors because the large molecules of direct dyes can actually penetrate the damaged areas of the hair shaft resulting in the permanent staining of the damaged areas.

Semi-Permanent Hair Color

Semi-permanent hair colors can use a cationic basic dye of small molecular structure. The small dye molecules penetrate the cuticle and rest on the surface of the cortex. Because these dyes actually penetrate the cuticle, they last up to 12-washes. A downside of small molecular dyes is that they can be washed off the surface of the cortex. Semi-permanent hair colors use no oxidizers, very little alkali and do not require mixing. Being free of oxidizers and low in alkalis, semi-permanent hair colors are considered much safer than permanent hair colors. Semi-permanent hair colors are most likely to be considered green or organic and the cationic dyes can be derived from plants or minerals.

Demi-Permanent Hair Color

Demi-permanent hair colors are similar to semi-permanent hair colors in that they both use basic dyes of small molecular structure. In demi-permanent hair colors, much more oxidizing agent is used than in semi-permanent hair colors. An oxidizing agent such as hydrogen peroxide can be used to damage and soften the cuticle and the cortex so that the basic dyes can be attached or bonded to the damaged areas of the cuticle and cortex. Small molecularly structured cationic basic dyes can penetrate the cuticle and do not require an alkali so the opening of the cuticle is minimal, resulting in less damage. Demi-permanent hair colors are usually classified as deposit only hair colors and used mostly when a darker color shade is desired.

Permanent Hair Color

Permanent hair colors are considered the most complicated and produce the best hair coloring results. Permanent hair colors are classified as "professional" and should be applied by a trained hairdresser. Permanent hair colors use oxidation dyes that react with an alkali and oxidizer. Oxidative dyes are small molecularly structured dyes that require an alkali to open the cuticle so that the dye molecules can reach the cortex. An oxidizer such as hydrogen peroxide can serve several purposes. The hydrogen peroxide dissolves the cortex and exposes the melanin or existing dye molecules, depending on its strength. Hydrogen peroxide also acts as a catalyst to process and expand the size of the oxidative dye molecules once inside the cortex. The expansion of the physical size of the oxidative dye molecules can actually prevent them from escaping back through the cuticle scales, making their attachment within the cortex permanent. The only way of removing oxidative dye molecules from the hair shaft is to chemically open the cuticle using an alkali and dissolving the dye molecule with the use of an oxidizer. Permanent hair colors can be classified as lift and/or deposit hair colors and can have a pH of 7.0-8.0.

Permanent Bleaching Hair Colors

Permanent bleaching hair colors work on a different concept than traditional permanent hair colors but last just as long. Ammonium persulfate salt (hereinafter, "bleach") is a high-potency oxidizer that is much stronger than hydrogen peroxide. Both hydrogen peroxide and bleach can be used together to produce a very potent oxidizing solution. This solution produces fact-acting results capable of quickly dissolving the cortex and melanin. Direct or basic dyes of small molecular structure are deposited deep within the cortex to create a long-lasting toning effect. Bleaching hair colors can cause the most damage to the hair's structure and caution must be used when applying them. Bleach can actually dissolve the entire hair shaft causing the hair to break or become severely damaged beyond repair. Bleaching hair colors are generally classified as lift colors and used to create light hair color shades. Bleaching hair colors can have a pH of 9.0-11.0.

Permanent Hair Coloring Forms

Permanent hair coloring products come in two basic physical forms, powders and paste-like creams. These products are considered complex blends of many ingredients that undergo extensive processing and blending to produce a final formulation. A typical cream formula includes water, surfactants, emulsifiers, solvents, purifiers, ammonia and hair dye. In general, water makes up 64% of the total weight percentage, surfactants 14%, emulsifiers 9%, solvents 6% and purifiers 0.3%. Together, these ingredients make up about 93.3% of the total weight of a typical permanent hair color formula, leaving only about 6.7% of the total solution's weight for oxidation dye coloring agents and ammonia.

Permanent hair coloring products are challenging to manufacture in a powdered state because it is difficult to accurately blend solids compared to liquids, resulting in less effective formulas. In some cases, powders can be manufactured by dehydrating once liquefied hair color formulations, but again, their quality and performance can be greatly diminished.

Permanent hair coloring products made with oxidation hair dyes are sometimes named oxidation hair colors because of this component. Most permanent hair coloring products are offered in a paste-like consistency called a "cream color." Cream colors can be packaged in metal tubes, similar to toothpaste.

Oxidation dyes make up less than 6.7% of a typical permanent hair color formula, but they are the most important component in the formula. Oxidation dyes consist of two primary parts: the precursor and the coupler. The precursor is considered the base of the formula. The precursor produces the deeper shades of hair colors. Examples of precursors include Phenylenediamine, Toluene-2,5-diamine, Methoxy-p-phenylenediamine, Chloro-p-phenylenediamine, Aminophenol 1,4-Diaminobenzene and 2,5-Diaminotoluene. The coupler produces the lighter shades of hair colors. Examples of couplers include be Resorcinol, Naphthol and Hydroquinone. When mixed together, a precursor and coupler form the basis of an oxidation hair dye. There are many precursor and coupler combinations possible and each can produce a different color or shade.

Both the precursor and coupler are highly unstable components that are prone to manipulation by their surroundings. Each can be chemically and physically altered when coming in contact with oxygen. These components should be protected from environmental conditions until they are ready to use.

A permanent hair color formula can also include a blend of inactive ingredients held in suspension within a tube. The process of using the hair color requires the hair colorists to squeeze a portion of hair color from the tube into a bowl, adding an oxidizing agent, such as hydrogen peroxide, and mixing thoroughly. Once the oxidizer, the activator or catalyst for the oxidizing process is introduced, the solution undergoes a chemical change that delocalizes the molecules first within the precursor and then the coupler. This delocalizing of the dye molecules combined with an external light source is the primary producer of the range of hair colors we see.

This activation process represents a drastic chemical reaction and time is now of the essence. Each oxidation dye molecule begins to grow in physical size as it consumes the oxygen and fuses with the other ingredients. This chemical reaction simultaneously causes the activated solution to weaken over time so the hair colorist must compensate and account for this during the application process.

Industry Problems and Challenges

The hair coloring industry has been plagued with many problems. Although many years have passed since the invention of viable commercial hair coloring products, they have and continue to be far from perfected. Existing problems range from clashing ingredients, manufacturing challenges, corporate domination and a lack of education. It's this same scenario that invites us in to repair these many flaws but each must be looked at closely.

Education Gap

The hair color industry struggles when it comes to education. A major reason for the education gap is because hairdressers and home-based clients do not understand the chemistry and mechanics behind the hair coloring process. Most depend on following the instructions provided by the hair color manufacturers and are lost without them. The dependency by end-users on instructions greatly limits their ability to correct or troubleshoot unwanted conditions or effects because they lack the experience and knowledge to modify the hair coloring process or chemistry.

Many existing hair-coloring products do not work as intended, making their instructions inaccurate. These same instructions are assuming a certain set of guidelines at the start, such as either clean healthy non-colored hair or previously colored hair with minimal damage. There are many variables that will greatly alter the outcome of a hair color procedure that are not addressed in the instructions. Once a permanent hair coloring process is started, there is no turning back. Sometimes it's a guessing game of what will be uncovered during the lifting process. Many hair colorists get into trouble after starting the permanent hair coloring process and often uncover problems.

The international system in place for measuring the shade of hair and hair colors is called the level system. The level system was created as a reference to follow so that all hair colorists around the world could have a universal way of determining the shade of hair. The level system is a shade scale ranging from 1-10 with 1 being the darkest shade and 10 being the lightest shade.

The level system immediately had problems when some hair color manufacturers called their darkest shades level 0 and others called their lightest shades 12. Dye color shades between manufacturers can vary greatly when compared to the universal level system. One manufacturer's hair color shade can vary as much as 2 digits thus making it virtually impossible to get the same results if you use another manufacturer's hair color brand. Manufacturers also produce different strengths of hair color formulas so you may need more of one manufacturer's color than another's. In addition to different formulas, manufacturers provide no means to precisely measure the ingredients. Manufacturers have made it as difficult as possible to succeed with hair colors. Some believe that the lack of transparency in ingredients and non-compliance with the level system is a deliberate attempt to sell more hair color by hooking the user and locking them into a commitment in fear of starting over with another brand.

Cosmetology schools are directly impacted by the hair color manufacturers' quest for sales. Manufacturers often offer the owners of schools a cash reward or deep discounts in return for loyalty. As each student is trained in hair color, they are also being introduced to only a certain brand of hair color. Most students never get the chance to learn the fundamentals of the hair coloring process because the manufacturer is only concerned about teaching their specific brand and students are only provided the instructions related to that brand.

Cosmetology teachers are in an awkward position because they are unable to teach the student the critical fundamentals of hair coloring. Without this knowledge, the students are sent into the work force without the ability to produce an adequate income so many end up sweeping floors and are expected to learn the techniques of coloring hair from other hairdressers.

Hair Colorists are simply not being supplied with the proper tools in which to succeed. It may be difficult to change an entire industry's mindset, but this disclosure is a step in the right direction, by creating products that work properly and predictably.

Tone Changes

The physical hair shaft goes through a dramatic transformation once an oxidation hair dye solution is applied by the hairdresser. The cuticle is softened and opened by the alkali, the oxidizer manipulates the polypeptide bonds, dissolves the cortex and either removes the melanin/dye or deposits new dye. The process of either lifting or depositing color within the hair shaft requires knowledge and precision.

When the hair shaft is lifted, it goes through a dilution process where melanin is first removed followed by preexisting hair dyes. Melanin is naturally dissolved by oxygen so it's easier to remove. Dyes are foreign matters consisting of either organic or synthetic formulas, so they take longer to dissolve. The lifting process takes hair through a gradual shade changing process thus revealing underlying tones. Color in general is a combination of the three primary colors: red, blue and yellow. Every color we view is a different combination of these three primary colors. This is most often viewed on a color wheel. Any portion or part of the total formula of three primary colors is known as an undertone.

During the hair color lifting process, all color undertones are exposed within the cortex. These undertones are often a combination of natural melanin, remnants of hair dyes left behind from prior hair coloring services or large molecularly structured basic and direct dye that have reached the cortex through hair damage. Traditionally, the closer the hair shaft is to the scalp, the more natural melanin is present due to the root grow out process. As you extend further from the scalp, chances are better the hair shaft was previously colored, processed or bleached by the sun so less melanin and more dye is present.

The manipulation of these undertones is vital throughout the process of changing the color of hair. Some undertones may not be wanted and some may be required. The cortex can only hold so many undertones before it's considered full. Once full, it is impossible to add more dye to the cortex so often undertones require removal from the cortex before new dye is deposited. Bleach is sometimes used to strip the hair of these unwanted undertones before oxidation hair colors are used, but in most cases, the oxidizer ratio in lift and deposit hair colors provide the proper amount of undertone removal. All oxidation hair colors undergo a working cycle. This working cycle is critical in managing undertones. An exact balance of heat, time, pH and oxygen is required so that undertones may be added or removed.

Unfortunately, the existing oxidation hair colors used from the tube can't achieve this delicate balance. Some reasons for this are directly related to the premature activation of these solutions resulting in a shortened working cycle, higher pH levels and a lowered amount of deposited dye. If an oxidation hair color does not complete the proper work cycle, it leaves behind unwanted undertones that clash with newly deposited dyes, resulting in drastic results such as bright orange hair. Orange hair is the direct result of a partially processed hair service or the lack of deposited dye (undertones).

People are living longer than before and more grey hair is observed. Grey hair is directly associated with age and many people are willing to spend money to hide their gray hair. The graying of the hair is the body's natural way of turning off melanin and natural oil production. Without melanin inside the hair shaft, all that can be visually seen is the mechanical structure of the hair shaft. With the lack of melanin and natural oil, the cortex collapses and takes on a non-healthy look and rough texture. Therefore, coloring grey hair is one of the greatest challenges that the hair coloring industry faces today and prior to this disclosure, no one has produced a hair color product that can work accurately and last on grey hair.

Damage

Hair coloring has become very popular and many people color their hair. Many hair coloring options are available, and the type of product chosen usually depends on the cost a person can afford. Traditionally the lower the cost, the less effective the hair color application. Some people can't afford to pay the high cost of a salon hair service, so they purchase home hair coloring kits and apply the hair color themselves. Some people purchase bleach and apply a self-made solution at home to lighten their hair in a cost-effective manner. For those who can afford a professional hair service, they face the difficult task of finding a qualified hair salon. Hairdressers struggle and even the best have failed many times and learned from their own mistakes. When you combine all these factors with the difficulty level of applying hair color correctly, there are a lot of people walking around with damaged hair.

Qualified hairdressers often get calls from new panic-stricken clients that just damaged their hair and need to have it repaired. The best hairdressers can repair damaged hair, but they require several visits and many hours of processing time. Now more than ever is the need for permanent hair coloring solutions that work correctly and are easy to use.

It is important to keep in mind that most of the chemicals used to permanently color hair are considered toxic and this is the main reason that the most powerful toxic ingredients must be applied by a trained professional. The Food and Drug Administration (hereinafter, the "FDA") sets industry standards and safety levels for each of the ingredients used in hair color. These guidelines are meant to protect clients from over exposure to dangerous chemicals.

The safety system put in place by the FDA is not perfect. Its primary flaw is the assumption of the amount of ingredients used in a single hair color application service. Existing hair coloring products are oftentimes so ineffective that hairdressers apply two to three times the instructed amount of hair color so that they can get it to work properly. This act doubles or triples the amount of toxic chemicals being applied to a client's scalp. The FDA standards set for a specific volume of hair color product are often breached through the over application of hair color product, leading to an unsafe level of toxic chemicals being applied on human skin.

Manufacturing Challenges

The process of manufacturing permanent hair color is challenging because the components used to make permanent hair colors are complex, unstable and often non-compatible. A primary mission of hair color manufacturers is to blend all the components in a ready to use package that is easy to use. Hairdressers are not chemists and due to safety reasons, manufactures are left with no other option but to premix and package these hair-coloring solutions in advance.

Permanent hair colors can comprise several complex ingredients. Many of these ingredients are either non-compatible or unusable in their physical raw form so they need to be blended using several different processes. Most hair coloring solutions are heated and combined with emulsifiers, surfactants and solvents to create a specific blend and consistency. Once a permanent hair-coloring solution is blended, it becomes very unstable and must be packaged immediately. Oxidation dyes, by nature, are starving for oxygen and will attempt to draw it in from every available source. Once introduced to oxygen, an oxidation dye solution begins the oxidizing process, which activates the ingredients within the solution. Manufacturers can add oxidizing inhibiting chemicals such as reducing agents and antioxidants but unfortunately oxygen is everywhere and it's difficult to prevent minimal oxygen contamination.

The process of manufacturing permanent hair colors creates many health concerns due to the heating and blending of hazardous ingredients. Ammonium Hydroxide and PPD are known skin irritants. Cocodiethanolamide (hereinafter, "cocamide DEA") is a known carcinogen used in emulsifiers. These ingredients are heated and blended before the user opens the package. What was intended to be a safe hair color formulation may have changed its chemical structure while resting in the package (tube) if the slightest bit of oxygen was introduced during the mixing and packaging process.

Oxygen Contamination

There are several components used to manufacture permanent hair colors. Manufacturers face a challenge because some of the components are chemically reactive, making it undesirable for them to be mixed prior to the time of use. Manufacturers have no option but to pre-mix these chemically reactive components because it would become very challenging for the hairdresser to mix these dangerous chemicals without the proper knowledge, equipment and expertise.

Manufactures are forced into blending together conflicting components in hopes of producing a usable product with minimal side effects. Most permanent hair coloring solutions are very similar. One manufacturer often produces several different brands by simply tweaking the same formula or adding a different label.

Oxidation hair dyes use oxygen as a catalyst. A chemical reaction takes place when the precursor, coupler or alkali blend is introduced to oxygen so every effort should be made to separate the components from each other and/or oxygen prior to use by the applicator. Unfortunately, manufacturers fail to follow these procedures and purposely introduce oxygen into the solution prior to packaging. Oxygen is present in the air during mixing and packaging, in the ingredients used to manufacture the hair color and even in the metal tubes used to package the solution. Since the primary ingredient of permanent hair colors is water (64%), it's a major source of contamination. Water ($H_2O$) is made of 1-part Oxygen. Even if water is distilled or deionizer and becomes $ddH_2O$, it still holds an oxygen molecule. There are processes to remove oxygen from water but when it's done, the resulting solution becomes very corrosive and should not come in contact with metal. This corrosive water solution can't be mixed or packaged with traditional stainless-steel equipment, so manufacturers prefer to keep the oxygen in the water.

Water is a major contributor to the contamination of permanent hair color solutions. When combined with all other forms of contamination during the manufacturing process and pre-use storage, it's proven that existing oxidation hair dyes have begun the process of oxidizing before they are purchased. Other professional hair color manufacturers have confirmed that permanent hair colors (cream colors) only have an effective shelf life of three years because of premature contamination. This information is not shared with the purchasing hairdressers, so they are unaware of premature degradation of their products.

Mutation

Permanent hair color (cream color) formulations are developed for a specific purpose and each ingredient plays a vital role in successfully coloring hair. If the original formula is altered in any way, the side effects can become enormous.

Oxidation dye is the key ingredient used in permanent hair colors. The average size of the raw form oxidation dye molecule can be about 5.15 angstrom, but if prematurely activated while in the package (tube), an oxidation dye molecule can begin developing and increase in size to over 8 angstrom. An oxidation dye molecule sized to reach the cortex may be too large to reach the cortex if it begins developing while in the package. Because the oxidation dye molecules are often developed and larger than intended, cream color formulations must compensate by using a higher pH or more alkali to open the cuticle wider to allow the larger dye molecules to pass through the cuticle. This approach can lead to increased damage to the hair shaft. Oxidative dyes also have an effective life span and since they have been prematurely activated, their effective life span is greatly reduced.

Once an oxidation dye molecule has been activated, it needs to expand and attempts to color hair as intended. When contained within a tube, the components begin the process of degeneration that leads to the most dominate chemicals becoming stronger and the less dominate chemicals becoming weaker. The alkali within the solution chemically changes, increasing in pH while the aminophenol weakens, producing less effective color deposit. This action greatly changes the properties of the hair coloring solution. What started out as a specific hair color formulation has mutated into a different hair color formulation, resulting in a less effective formulation that will produce very different hair color results than originally intended.

Side Effects

Manufacturers provide instructions with their oxidative hair colors and base these instructions on ideal conditions. Since the hair color chemically changes due to premature activation, the instructions are not accurate when used. Hairdressers are being forced to use the wrong product without accurate instructions. This scenario is the leading cause of bad hair coloring results. Since hairdressers are forced to use the wrong hair-coloring product from the start, it is vital to understand what they are actually using and how it reacts with the hair shaft.

The mutated oxidative hair color has changed its chemical structure. The pH usually has risen by 1-2 digits, the oxidative dye molecules have increased in size and the solution has weakened. When this solution is applied to the hair shaft, the cuticle is opened wider than intended and the oxidative dye molecules are less able to penetrate the cortex. Effective processing time is also reduced due to a prematurely weakened product.

When a hairdresser uses this mutated hair coloring solution, they must use great caution. The potential of hair damage is increased due to the higher pH, less deposit and decrease in processing time. Hairdressers are forced to apply two to three times the normal amount of hair color to create an effective hair color process on their client, thus exceeding the safety limits set by the FDA.

Disclosure

The disclosure herein includes an additive for use with a donor hair color product or formula to create a mixture, comprising a plurality of raw oxidation dye molecules and an excipient. In some embodiments, the disclosed additive comprises raw oxidation dye molecules that comprise a coupler and precursor. In some embodiments, the raw oxidation dye molecules comprise a size of less than 6.2 angstrom at the time of application. In some embodiments, the additive is configured to control the speed and delivery of all molecules and chemicals comprising the mixture.

The disclosed additive can be configured to do one of blocking, metering or screening unwanted chemical components of the donor hair product from entering the mixture. In some embodiments, the additive controls the speed and flow rate of oxidation dye molecules. The disclosed additive can be configured to encapsulate at least one unwanted chemical component of the donor hair product from entering the mixture.

In some embodiments, the disclosed additive is configured to dismantle at least one unwanted chemical component of the donor hair product and salvaging usable parts of the unwanted chemical component, while discarding unusable parts of the unwanted chemical component. The excipient used in the disclosed additive can comprise a polysaccharide. In some embodiments, the additive further comprises a surfactant. In some embodiments, the additive further comprises a solvent. In some embodiments, the raw oxidation dye molecules further comprise packaging in an environmentally secure atmosphere with a single dose of 0.001-0.321 grams and wherein the excipient further comprises packaging in an environmentally secure atmosphere with a single dose of 0.020-0.060 grams. The disclosed additive can comprise one of a solid, powder, liquid and a combination of a solid, powder and liquid.

This disclosure also contains a method of coloring hair, the steps comprising: providing a solution with a pH level that causes a cuticle layer of a hair shaft to open by 7 angstrom; providing a solution containing raw oxidation dye molecules comprising a size of less than about 6.2 angstrom in the solution; allying the solution to the hair shaft and causing a cuticle layer of a hair shaft to open a plurality of scales to 7 angstrom; allowing the raw oxidation dye molecules to pass through the cuticle and into one of the cortex and medulla of the hair shaft; enlarging the raw oxidation dye molecules located in one of the medulla and cortex by oxidizing them within the medulla and cortex, causing them to grow in size to larger than 5 angstrom; stopping the hair coloring process and closing the cuticle of the hair shaft; and trapping the raw oxidation dye molecules in the medulla and cortex. The disclosed method can include wherein the raw oxidation molecules comprise a coupler and precursor. The disclosed method can include wherein the solution is configured to control the speed and delivery of all molecules and chemicals comprising the solution. The disclosed method can include wherein the solution is configured to do one of blocking, metering or screening unwanted chemical components of a donor hair product from entering the solution. The disclosed method can include wherein the solution controls the speed and flow rate of oxidation dye molecules.

The disclosure contains a method of coloring hair, the steps comprising: selecting a donor hair coloring product; determining a client's existing hair color level and condition; using a predetermined chart to determine the available new colors available to the client; using the predetermined chart to determine the amount of an additive to mix with the donor hair coloring product; mixing 30 grams of the donor hair coloring product and the additive; and applying the donor hair coloring product and additive mixture to the client's hair. In some embodiments, the predetermined chart further comprises a computer implemented software-based chart.

BRIEF DESCRIPTION OF THE DRAWINGS

FIG. 1 is an example chart provided to show a method of using the disclosed additive in a safer and more precise hair coloring process, when combined with a donor or existing hair coloring product.

DETAILED DESCRIPTION

The present disclosure includes an additive comprising at least a raw unoxidized oxidative dye or formula consisting of a precursor or coupler or any combination of both and an excipient (hereinafter, the "additive"). The additive can be used with an existing commercial hair coloring product or chemical formulation capable of coloring hair hereinafter, (a "donor" or "donor product") using the methods disclosed herein. In some embodiments, the additive can be used as a hair color product without a donor product. A "donor" or "donor product," as used herein, refers to any existing hair color product or chemical formulation capable of coloring hair, however manufactured. A donor or donor product can be sacrificed, altered, modified or dismantled to salvage it's usable parts. A "donor" or "donor product" can include, for example, temporary hair color, semi-permanent hair color, demi-permanent hair color, permanent hair color or bleaching hair color.

The oxidation dyes used in the additive can be in their rawest and smallest form, making them small enough to pass through the cuticle and the cortex. Oxidation dyes are unique in that they are not complete in their raw form. Oxidation dyes comprise two parts: a coupler and precursor (intermediates) and may not hold the capacity to color hair in their raw state. An oxidation dye molecule in its raw state, as used herein, refers to an oxidation dye molecule in a plurality of components that need to be combined to form an oxidation dye molecule. For example, an oxidation dye molecule in its raw state can be a coupler and precursor waiting to be built into an oxidation dye molecule. Coupler and precursor molecules are very small in size and are able to penetrate the cuticle of the hair.

The building process of an oxidation dye molecule starts by exposing the oxidation dye molecule in its raw state to oxygen. Oxygen is the catalyst that sets off a chemical reaction that builds the oxidation dye. The process delocalizes the molecules first within the precursor and then the coupler. This delocalizing of the dye molecules combined with an external light source is the primary producer of the range of hair colors we see. This chemical reaction causes the oxidation dye molecules to grow in physical size thus making them more difficult to handle and apply.

This disclosure is focused on the use of oxidation dye molecules in the cosmetic industry, but they can be used in other industries, such as the fir, leather and beauty industries. The disclosure herein enables the use of oxidation dyes in hair coloring products, but the disclosure is not intended to limit their use in other industries or applications.

Oxidation dyes can also be fragile because they chemically transform from small molecular structures into large molecular structures through the introduction of a catalyst, such as oxygen. The process of delivering oxygen to the oxidation dye molecule is critical to the performance of the dye. The amount of oxygen delivered and the timing of when it is delivered greatly alters the reaction and performance of each dye molecule. It is not uncommon to have two identical oxidation dye molecules reach a different size and produce a different color tone based on the way oxygen was delivered.

There various oxidation dye intermediates and each holds different characters and molecular sizes that act differently when exposed to oxygen. Table 1 is a partial list of possible oxidation dye intermediates that can be used in some embodiments:

TABLE 1

| Oxidation Dye Intermediate | Color(s) |
|---|---|
| p-Aminophenol | Golden Brown |
| o-Aminophenol | Golden Orange |
| 4-Amino-2-methylphenol sulfate | Red Brown |
| 4-Amino-3-methylphenol | Light Grey, Brown |
| 4-Amino-2-nitrophenol | Red Brown |
| 2,4-Diaminophenol hydrochloride | Light Red Brown |
| 4-Chloro-2-aminophenol | Grey Yellow |
| 4-Nitro-2-aminophenol | Bright Yellow |
| 4,6,-Dinitro-2-aminophenol | Dark Orange |
| 6-Chloro-4-nitro-2-aminophenol hydrochloride | Dark Orange |
| p-Phenylenediamine | Black |
| o-Phenylenediamine | Yellow |
| p-Toluylenediamene | Medium Brown |
| o-Toluylenediamene | Golden Grey Brown |
| 3,4-Toluylenediamene | Golden Brown |
| Choloro-p-phenylenediamene sulfate | Red Brown |
| 4-Choloro-o-phenylenediamene sulfate | Brown Gold |
| Nitro-p-phenylenediamene | Dark Red |
| 4-Nitro-o-phenylenediamene | Red Orange |
| 5-Choloro 3-nitro o-phenylenediamene | Orange |
| 1,2,4,Triaminobenzene dihydrochloride | Deep Black |
| p-Aminodimethylaniline | Oxford Grey |
| p-Aminodiphenylamine | Blue Black |
| 4-Aminodiphenylamine | Brown Black |
| 2,4,Diaminodiphenylamine | Brown Black |
| 4,4,Diaminodiphenylamine | Brown |
| 2-Aminodiphenylamine | Grey Red |
| 4-Methoxy-4-amino-diphenylamine sulfate | Light Ash |

The raw size of each oxidation dye molecule plays a vital role in the disclosure herein. Oxidation dye intermediate molecules can range in size from 4.7 angstrom to 6 angstrom.

1 angstrom=10-4 micrometers um=0.1 nanometers nm=100 picometers pm

Once activated by the catalyst action of oxygen these same oxidation dye molecules grow and expand in size to well over 0.8 nanometers nm. The actual size reached is dependent on several factors that include, the amount of oxygen present, time in contact with oxygen, heat, moisture content and the dye formula used.

Carrier solutions are a chemically neutral base medium used to suspend and deliver active ingredients in a precise manner. They can be used to bulk up a chemical formulation so that it can be measured correctly and administered in a timely manner. Examples of carrier solutions are excipients. Various suitable excipients can be used in the additive, depending on the physical structure of the chemical formulation. This disclosure focuses on a dry powder formulation but some embodiments can use non-powder based excipients, such as, for example, a liquid based excipient. Some excipients that are particularly suitable for the additive include antiadherents, binders and disintegrants. Lactic acid is a carrier solution that manipulates pH and polysaacharides can hold special targeted features when used in cosmetic production. The term, carrier solution, as used herein, can include any chemical medium used to suspend and deliver active ingredients in a mixture of components. The term, excipient, as used herein, includes any antiadherents, binders, disintegrants, polysaccharides or and/or lactic acids. The polysaccharide family is made up mainly of starch, starch sugars and modified starches. These large molecular chained substances can be made from plants and vegetables such as potato, wheat, rice, corn and tapioca.

In some embodiments of the additive, the large molecular chain structure of polysaccharides is used to shield or encapsulate unwanted chemicals found in the donor product. The polysaccharides can be used to encapsulate residual toxic residues, keeping them from contacting the scalp during and after a hair coloring service. In some embodiments, the polysaccharides can be used as a shield or filter for unwanted hair dyes.

Modified starches can be custom built to perform many duties and included in some embodiments of the additive. Some embodiments can comprise modified starches to regulate pH levels and/or work as a reducing agent.

In some embodiments, the additive can further comprise surfactants and solvents. There are several families of surfactants, including, but not limited to, anionic, cationic, zwitterionic, nonionic and biosurfactants. A primary difference with each family of surfactant is the polarity of their molecular heads. Each family of surfactant blends differently in a chemical formulation based on the polarity of the chemical it is attaching to.

Some embodiments of the additive comprise a surfactant that can assist with controlling the speed and flow (delivery) rate of the chemical formulas. The use of a surfactant can allow some components to be delivered faster, slower or blocked completely. Surfactants can also be used to salvage chemical parts from the donor product and/or control pH levels. In some embodiments, the surfactant can maximize or minimize the amount of hair dye produced by each oxidation dye molecule and/or the breakdown of toxic residues.

Solvents can come in many physical forms such as liquids, oils, powders and solids. Some examples of solvents include, but are not limited to, ethanol, acetone, ethylhexyl palmitate and esters. Some embodiments of the additive comprise a solvent that can be used to control the consistency of the chemical formula and/or to breakdown the chemical formulas of the donor product.

A particularly effective family of solvents for use in the additive is Solvent Violet 13 ($C_{21}H_{15}NO_3$). This family of solvents includes solvents such as D & C Violet No. 2, oil violet, Solvent Blue 90 and Disperse Blue 72. These solvents are formulated using synthetic dyes to form a blue or violet toned solvent. In some embodiments, Solvent Violent 13 can be used as a key-toning component or a platinum series (e.g., a hair color with a pure silvery white appearance and generally lacking traces of brown and/or orange) of the invention.

The additive disclosed herein preferably comprises raw oxidative dye molecules and a carrier solution comprising an excipient. In some embodiments, the additive comprises 4-85% oxidative dye molecules by weight. In some embodiments, the additive comprises 10-96% carrier solution by weight. In some embodiments, the additive further comprises a surfactant. In some embodiments, the additive further comprises a solvent.

The additive disclosed herein, when combined with a donor product, prevents a mutated donor product from clogging the cuticle and causing undesirable hair coloring effects. The oxidation dye molecules in the additive are non-oxidized, making them smaller than the mutated and oxidized dye molecules in the donor product. The additive only opens the cuticle the minimum amount to allow the oxidation molecules of the additive to pass through, preventing unnecessary damage and blocking the enlarged donor product molecules from clogging the cortex. In some embodiments, the additive slows the donor product's oxidation dye molecules and speeds the diffusion of the additive's oxidation dye molecules into the hair shaft. The additive also breaks down the cortex allowing the additive's oxidation dye molecule to pass into the cortex and into the medulla. Once in the cortex and medulla, the additive's oxidation dye molecules go through the oxidation process and grow in size, trapping them within the cortex and medulla permanently. In some embodiments, the additive's oxidation dye molecules grow from about 5 angstrom to about 8 angstrom after the oxidation process.

The manufacturing process and packaging for the additive are also significant parts of this disclosure. The manufacturing process for the additive is preferably completed in a low oxygen environment to reduce the oxygen content in the additive, making it more stable and preventing pre-use mutation. The additive can be manufactured in a chemical formulation that takes the form of a solid, liquid or any combination of these physical forms. The oxidation dyes used in the additive can include basic dyes, direct dyes, cationic dyes and any combination of these dyes, along with any future or past dyes that have or effectively will color hair.

The manufacturing process for the additive is focused on creating a packaged product that does not react in the package prior to use. Each specific hair color variation or additive intended for a specific donor product may have a specific chemical formulation to avoid pre-use chemical reactions in the package. Each formulation can be specifically developed to achieve a certain chemical reaction or result. Some chemical combinations can achieve only color tonal changes while others can target pH balancing in order to color hair. The chemical formula of the additive generally performs at least some of the following tasks:

(a) Maintains a low oxygen content in the formula so that the formula remains stable and uncontaminated.
(b) Acts as a carrier or delivery formulation in which to deliver precise amounts of hair dyes in a measurable form.
(c) Control the speed, flow and accuracy of hair dye delivery.
(d) Manage the pH level to control and manipulate the hair cuticle's mechanical functions.
(e) Salvage or mask ingredients from donor hair coloring products.
(f) Clean, encapsulate or contain toxic residues left behind during the hair coloring process.

The package forms a vital part of the presented invention as it is much more than just a retail package. Most of the chemical formulations disclosed in the above description are very small in physical size and very chemically unstable. The package generally has at least some of the following properties:

(a) Be made in several precise sizes and act as a measuring device to aid in both the manufacturing and application process.
(b) Be made of materials that form a shield or barrier to protect the chemical formulation from sunlight, moisture and atmospheric contaminates such as oxygen.
(c) Contain chemicals in any physical form that hold inert, reducing or antioxidant properties.

There are various types of packages capable of performing these duties but the most suitable include a sachet, bottle, vial, capsule or tablet placed in a sealed tray.

Some embodiments of the additive are packaged in small vials or bottles. Small vials or bottles can be a viable option when handling liquids and powders. In some embodiments, the small vials or bottles comprise dark shades of glass or plastic. A glass bottle is preferred for maintaining a sterile environment, but plastic could also be used adequately. The vials or bottles could comprise any appropriate size to aid in measuring and any shape to assist with application. Closures could include screw-on or snap-on caps or just plastic or foil sealed films.

Capsules are another option when handling powders. They are produced in two halves and can be made in any size and depth. Capsules can aid in precise measuring and application and can be made from pharmaceutical grade materials.

Solid tablets or pills are again another option, as they are easy to manufacture, handle and apply. Tablets can be coated with a pharmaceutical grade coating such as glyceryl behenate that can act as a dissolvable atmospheric barrier. In some embodiments, solid tablets may be ground into a powder as part of the application process.

Sachets or bags may be used with powders or solids. These can be manufactured in many sizes and be manufactured from many materials to aid in creating an atmospheric barrier that can shield from light. With the aid of machinery this can be the fastest and most precise means of measuring and delivering the chemical formulations.

Trays with recesses or receiving pockets may be used to contain solid versions of the chemical formula such as pills or tablets. They may also be used to hold individual pre-made capsules in order to insure ease of application. Trays may also be used as a secondary atmospheric barrier thus making two barriers when combining a capsule or coated tablet.

Any of the packaging options disclosed herein can also contain inert properties in some embodiments. Chemical such as inert gasses, noble gasses, antioxidants and reducing agents can be inserted into the package or chemical formula itself.

It is further intended to make the invention easy to use. Hairdressers are not chemists, so a platform has been created to instruct them on how to use the disclosure in a simple manner. Each packaged chemical formulation will become easily identified and aligned with a chart or computer software program. An example would be:

| Formula A | Capsule | Green Color | #3 |
| Formula B | Tablet | White, Blue Stripe | B |
| Formula C | Sachet | Silver | Step 1 |

Method of Use

The additive disclosed herein can be used in the method disclosed herein to provide a highly accurate method of coloring hair using existing donor products. The first step in the method is to chart a client's hair using the chart 10 in FIG. 1. While the chart 10 is being provided in a printed format in FIG. 1, it can also be provided electronically through a software program or application to a user. The charting element gathers information about every aspect of the hair coloring process, including:

(a) Condition of the client's hair before coloring
(b) Hair coloring products used in the past
(c) Heath screening for allergic reactions
(d) Amount of grey hair present on the client and what level it is
(e) What hair color level the client is now
(f) What host or donor product will be used
(g) What hair color the client wishes to achieve For clients with grey hair, it is important to start on the left column 11 of FIG. 1 to determine the grey tone and percentage grey hair that the client has. In the left column 11 of FIG. 1, levels 6 and 7 are for clients with 50% grey hair, level 8 is for clients with 75% grey hair and level 9 is for clients with 100% grey hair. The grey hair level determination should be completed at the root area of the hair for the most accurate results.

In some cases, clients with grey hair have darker non-grey hairs that must be accounted for. When clients with grey hair have non-grey hair with hair that is darker than level 5, they must be started at level 5 on the left most column 11 of FIG. 1.

For clients without grey hair, their hair condition evaluation begins on the "No Grey Level Scale" column 12 in FIG. 1. Using this column 12, it's important to determine what color the client's hair is starting at on the level system. Generally, hair can be colored 2 levels up or down the level system without an additional type of component to control unwanted pigments from lifting the hair.

Once the client's hair level is selected on the grey level scale 11 or the no grey level scale 12, the hairdresser looks to the right right across the table to see which colors are available for that client in area 13 of the chart 10. Area 13 of the chart 10 is populated with available colors 14 for that client based on the client's starting hair color and the donor product used for the chart 10. For each color available at that level, there is an additive level column for clients with 100% grey hair 15, 75% grey hair 16, 50% grey hair 17 and no grey hair 18. The number in the additive level column indicates the number of additive packs that are needed to achieve that color for that client. The chart 10 in FIG. 1 is an example for a single type of donor product and can be replicated for each type of donor product within the inventive concept disclosed herein. The additive packs identified on the right side of the chart 13 are preferably the same for each available hair color 14 that the client selects. The hairdresser would then select the additive for the color selected in the quantity identified on the right side of the chart 13 for the next steps. In some embodiments, the additive packs identified on the right side of the chart could be the same for different colors.

Mixing the Additive

The charting process indicates the amount and type of additive to use as ingredients for a particular hair coloring process. The components then need to be blended to produce the effective hair coloring solution.

The additive and method of use disclosed herein require a precise measurement of the chemical components. Many of the components included in the additive are less than one gram by weight and the only way to precisely measure them is through the use of a chemical scale or balance. An exact sized measuring cup can be used in some embodiments. In some embodiments, precisely sized packaging measures the chemical components for the user during the manufacturing process, allowing the user to avoid having to independently measure chemical components.

There may be several different physical types of ingredients used in a hair coloring formula. An example may include a liquid being blended with a powder and then added to a paste. Temperature may also play a vital role, as some ingredients blend better when they are warm or hot. Another closer example of a usable hair coloring formula would be blending a paste donor permanent hair color product with a liquid hydrogen peroxide and a capsule containing our chemical ingredients in powder form.

The amount of additive used is determined based on the charting step and 30 g (gram) of donor product. The type of donor product is considered in the charting step to determine the type and amount of additive used in the next steps. The use of 30 g of a donor product provides a good working amount of hair coloring solutions and the mixture of donor product and additive can be repeated, as needed, to complete a hair coloring process. It is generally better to freshly mix new batches of donor products and additives, as needed, rather than let a mixture sit for any period of time.

The 30 g donor product can be established by measuring 30 g of the host or donor product and placing it in a mixing bowl. The process of adding the physical chemical formula of the additive can be completed by either opening a capsule or sachet and pouring the contents into the same mixing bowl. The method can include adding a specified amount and proper level of liquid oxidizer such as hydrogen peroxide to the same mixing bowl in some embodiments. Another embodiment would include mixing any two components as a separate step then mixing the blended combination into the final components. All components are thoroughly blended until all they are dissolved and uniformly blended, starting the catalyst process of activating the ingredients.

Once the charted chemical formula of a donor product and the additive have been mixed, it becomes activated by a catalyst and transforms chemically, weakening over time. Once mixed, the solution is preferably applied to a client's hair as soon as possible.

Application

A typical client has root grow-out or colored their hair before. This creates different conditions for the hair coloring formula to color and each condition area is very much different. Add in the fact that the hair coloring formula created is gradually weakening over time and you have a problem to deal with. The major goal is to achieve uniform hair coloring results across the entire head while dealing with several variables.

Often hairdressers map out a client's hair coloring procedure, defining areas that will process quicker and those that don't. Processing is the actions of the hair color formula coloring the hair once activated by the catalyst, thus chemically changing the texture and color of the hair shaft.

The physical product of this invention often works in a different manner than traditional hair colors as the chemical ingredients are different and can process differently, thus altering the application process for the hairdresser. When using the disclosed additive, problem areas in a client's hair may no longer be problem areas. In some cases, multiple applications of the disclosed method may be required and sometimes, different chemical formulas will be required to address extreme changes observed from the root to the hair shaft end. Uniform hair coloring results are usually the goal and several options exist to arrive there.

It is a good practice to map out a hair coloring service and segment the hair into work zones before mixing the hair coloring solution. In many cases, there are different conditions on a client's scalp. A typical condition will involve newly grown hair at the root line followed by some hair that has previously been colored and followed again by some hair that may be damaged physically at the ends. In many cases, a different 30 g hair color formula and additive will need to be mixed to tackle each of these areas independently.

Once all the ingredients are blended and activated, they are applied to the proper segmented area of hair on the scalp using a typical applicator brush or wand. In some cases, foils are used to isolate certain strands of hair to provide for a more precise variegated outcome.

After application on the hair, the coloring solution is allowed to process chemically. This action transforms the hair shaft through multiple phases of processing, resulting in reaching its final desired effect. The applicator or hairdresser usually views the final phase of this process carefully to determine when it is finished.

The hair is then washed with water to stop the chemical reaction and continual coloring of the hair shaft. Processing aids, such as hair dryers, steamers and caps to increase the temperature, can be used to increase the processing speed of the hair coloring solution.

The outside layer of the hair shaft is covered with small scale like features called the cuticle. These scales open and close regularly based on the surrounding pH level. They act as a protective armor for the cortex that holds the vital components of the hair shaft such as melanin and protein chains. By nature, the cortex is considered 100% full of solids and liquids such as melanin, proteins, oils and salts. The cortex is in its healthiest state when there are no air voids or gas pockets. Permanent hair color processes structurally damage hair and every existing permanent hair color product fails to repair the structural damage that it causes to the hair.

The permanent hair coloring process begins by submitting the hair to an alkali such as ammonia to raise the pH on the cuticle thus opening it and exposing the cortex. An oxidizer such as hydrogen peroxide begins the process of dissolving and removing melanin, existing hair dye and some proteins from the cortex. Oxidation dye molecules are then deposited within the cortex and the cuticle is closed by lowering the pH level thus trapping the dye molecules inside the cortex.

The opening and manipulation of the cuticle is the single most important factor in hair coloring and holding the integrity of the hair shaft. The difference in opening the cuticle from 0.4 nm to 0.8 nm is dramatic when viewable physical hair damage can be noticed at 0.7 nm. In some embodiments, the additive opens the cuticle to about 0.6 to 0.7 nm, avoiding visible hair damage.

An alkali is the most common ingredient used to alter the pH level during hair coloring, but it must be used sparingly to prevent hair damage. A goal behind correct permanent hair coloring is to open the cuticle the smallest amount that is needed to perform the required duties. Opening the cuticle too much can cause damage, but if the cuticle is not opened enough, dye molecules cannot travel into the cortex. The cuticle is similar to a door that regulates the size of what passes through it.

The oxidation phase of permanent hair coloring is the process of dissolving and removing materials from within the cortex and carrying them through the open door (cuticle). After the oxidation phase, existing permanent hair coloring products leave voids and pockets lacking substance. In dry conditions, these voids and pockets become air or gas pockets. Hair after the oxidation phase becomes structurally damaged, weak, and prone to breakage because it does not contain uniform matter. If you viewed a cross section of the hair shaft it would look like a dried sponge. The additive disclosed herein can fill voids and repair the hair shaft after the oxidation phase.

The hair cuticle is then closed as the pH level drops either naturally or by promoting the process by applying a pH reducer. Once the cuticle is closed, the hair coloring process is considered complete.

The additive and method disclosed herein allow a user to manipulate and control the physical size of chemicals so that they can be placed into the cortex of the hair shaft in a certain order. The disclosure also includes the management of the opening width of the cuticle to align precisely with the size of chemicals that are intended to pass through its opening. Another aspect of this disclosure is to control and harness the diffusion process of hair-coloring chemicals.

Several components form the chemical formula of the disclosure and each has a specific purpose when applied to the diffusion process. These chemicals can be responsible for salvaging or blocking certain ingredients from entering the cortex and manipulating the physical size of others so that they may enter the cortex freely. When a chemical is blocked from entering the cortex, it may be used for a different purpose than originally intended or considered a waste residue.

Waste residues can be considered toxic and can be encapsulated or dismantled to prevent these toxins from coming in contact with the scalp, making the invention safer than other traditional permanent hair coloring solutions.

The additive disclosed, in some aspects, can balance the pH levels to control the amount the cuticle opens, aligning it with the physical size of oxidation dye molecules passing through its opening. This control over the cuticle will act as a screen or meter allowing only wanted dyes of a particular size to pass through the cuticle while preventing others of larger size. A mission is to harness the diffusion process of oxidation dyes.

Once the hair coloring oxidation process is complete, the hair shaft is left in a damaged condition. It's stripped of many essential physical elements thus leaving behind voids, enclosures and pockets. It is vital that each of these voids be refilled with matter. This is where all existing permanent hair-coloring products fail.

The primary reason they fail falls back on basic mechanics, you can't force a large item through a small opening. When this action is forced, the cuticle openings become clogged and block out key ingredients from reaching their destinations within the cortex. As pH levels drop, the cuticle clamps down on the clogged openings and never completely closes. With the cuticle openings clogged, the voids within the cuticle never get a change to be filled with matter.

This disclosure solves the problem of clogged cuticle openings by taking a new approach. The additive causes the cuticle to allow only certain sized chemical molecules to pass through the cuticle, preventing clogging and blockage. This ensures that every void is filled within the cortex by inserted a special blend of the ingredients of this invention.

The precise delivery of oxidation dye molecules into or onto the cortex of the hair is considered a foundation of this invention. This diffusion process begins by preparing each dye molecule for delivery by first maintaining its smallest physical state. In some cases, the dye molecules are inserted into the cortex in two parts and the dye molecule is built inside the cortex by activating it with an oxidizing catalyst.

This precise delivery of oxidation dye molecules in their smallest physical state is possible by handling and packaging the raw oxidation dye molecules in an inert state. Every effort has been made to prevent or limit cross contamination by preventing and limiting contact with non-compatible chemical ingredients such as oxygen. This chemical formula will only be added and mixed with the other chemicals of this invention during the last minute before application as a separate step.

Oxidation dye molecules are very small in physical size averaging 5.15 angstrom and the cuticle may be opened to 7 angstrom before damage is occurred. It is a balancing act to regulate pH levels and align them with the dye molecule sizes, but when done correctly the diffusion process is a success.

Once all the voids and pockets are filled within the cortex it is considered full and will no longer accept additional matter. The chemical blend inserted into the cortex is considered critical as it dictates the final color tone and physical strength of the hair shaft. The additive and method disclosed herein provide a system that allows a user to activate this reactive chemical solution inside the cortex and close the cuticle by lowering the pH level. The oxidation dye molecules continue to grow in physical size inside the cortex after they are activated, lodging and locking them in place.

The final step in the method is keeping the cortex closed by carefully monitoring pH levels. Another feature of this disclosure is as a hair color maintaining solution whereas the same formula can be used to color the outside of the hair shaft after a premium hair coloring process has been performed, this can be done by using the same product in a low pH environment. In some embodiments, the additive can be combined with a donor that is a temporary hair coloring product to provide a hair color maintaining solution to color the outside of the hair shaft.

Optional Uses

A unique feature of this disclosure is that a common cosmetic product or ingredient found on the shelf can be the actual catalyst used to activate the chemical reaction in the additive. Once activated by these common ingredients, the physical invention begins the transformation process. By nature, the suspended chemical formulation is starving for activating ingredients and begins the process of seeking them out by salvaging them from the host (donor product). This action transforms the host product by dismantling it and altering its chemical structure.

Timing is another key feature of the invention whereas each ingredient chemically processes at a different time and speed once activated and this action is responsible for generating different and unique color effects that were once impossible to obtain from traditional hair coloring products.

The most accurate way of understanding the invention is observing its actual performance within the cosmetic industry. As revealed, the invention can be used for multiple purposes but is primarily designed to tackle professional hair-coloring issues. It can be used as a temporary, semi, demi, permanent and bleaching hair color additive product. In each case the physical product works differently because of its chemical surrounding and specific requirements.

Temporary Hair Color

Because temporary hair colors do not use an oxidizer or alkali their pH level remains low and the hair coloring effects are contained to the outside of the hair cuticle. Usually small amounts of large molecular sized direct dyes are used within the formula. Many products within this class are considered temporary products such as low-grade hair colors, shampoos, conditioners and grooming products.

The additive disclosed herein can transform temporary hair color products into hair color maintenance products by allowing a customer to enhance and maintain a prior high-end hair coloring service at a low financial cost. In this case, a customer could apply a precise color tone on the outside of the cuticle that matches or enhances the underlying hair color tone that is embedded within the cortex. When applying color to the outside of the cuticle, it is critical to keep the pH low so that the cuticle remains closed and so that embedded dye molecules remain inside the cortex. The physical structure of the hair is also maintained with a low pH, thus creating a healthy shine.

Semi-Permanent Hair Color

Semi-permanent hair colors introduce small amounts of alkali and use small molecular sized cationic basic dyes. Semi-permanent hair color products are usually home hair coloring kits or marketed as having fewer toxic chemicals.

When the additive disclosed herein is used with semi-permanent hair color products, it can be used sparingly. This industry promotes a high level of health safety and minimal professional hair color application experience is present. Users often run into problems using these products so the disclosed additive can be used as a kicker, troubleshooter, color balancer or enhancer. This application uses the smallest doses of active ingredients to boost the safety aspect of the hair coloring solution, providing the ability to dissolve and isolate harmful hair-coloring ingredients.

Demi Permanent Hair Colors

As noted previously, demi and semi hair colors are similar, except for the introduction of small amounts of an oxidizer that is introduced into demi hair colors. This introduction of oxidizer greatly enhances the effects of demi hair colors and enhances the effect of the inventive additive when used with a demi-permanent hair color. Because demi-permanent hair colors are applied by professionals, the inventive additive can include more active chemical ingredients than when used in semi-permanent hair color applications.

When the additive is used with existing demi-permanent hair coloring products, a new and effective low-cost hybrid hair color is created. This hybrid demi-permanent hair color product combination lasts twice as long and more unique hair color tones are created.

The additive for use with demi-permanent hair colors can include blending oxidation dyes with the cationic basic dyes. Because both types of these dyes are small molecularly structured dyes, they are compatible. Very aggressive color tones can be created by blending both types of hair dyes but for the very first time these bold colors will last much longer.

Permanent Hair Colors

Permanent hair color products are meant for professional application and these donor products allow a user to realize the highest benefits of this disclosure. Permanent hair coloring products also use oxidation dyes, but in a contaminated and activated format that is largely ineffective at its intended purpose. In some embodiments, the additive blocks the contaminated and activated large oxidation dye molecules found in donor permanent hair color products to prevent them from clogging the cortex and/or the cuticle.

The ultimate goal of hair coloring is to create precise hair color tones that last the longest without damaging the structure of the hair. This is the greatest challenge that currently exist within the hair coloring industry besides coloring grey hair. Both issues are solved through this disclosure and new partnership of products.

Bleaching Hair Colors

Bleach is a powerful blend of oxidizer and alkali and when applied brings the hair up to a pH level of 10. Bleach quickly dissolves everything in its way and can dissolve the entire hair shaft if left unattended.

Bleaching hair colors are produced in the highest-level shades and usually range from 8-10. They work by stripping the hair of every trace of melanin and dye and replacing it with a strong synthetic basic dye that can hold up to this aggressive bleaching action. The additive disclosed herein can be used in a different manner than ever before to show its performance as a troubleshooter and secondary color enhancer.

Additive as a Repair Product

Hairdressers often run into complications using traditional hair colors. Each involves applying a specific amount of pre-formulated ingredients for a specific period of time. Generic conditions are assumed by the hair color manufacturer and their product ingredients are assumed to be at full strength and free of contaminates.

There are a variety of factors working against hairdressers when applying hair color to a client, as disclosed herein. Hairdressers only have one shot during a hair color process to get it right and if anything goes wrong, they can be stuck with a client having orange hair. Orange hair syndrome is actually a condition of under processed hair where the hair color formula has failed or weakened before reaching its mission.

A typical hair color process can last between 20-50 minutes depending on the color of the hair, condition of the hair and what color the client wishes to be. During this process, the hairdresser can view the chemical hair color working by seeing the hair transform through a series of color tonal changes. Professional hairdressers are trained and licensed and most have experience in hair coloring. A hairdresser can quickly realize when something is going wrong simple by viewing the hair coloring process.

In the past, when a hair coloring process went wrong, the hairdresser was left with no other option but to watch it fail. The additive disclosed herein can be added to the hair coloring process at the first sign of trouble, saving and enhancing the outcome.

Additional Data

Several versions of the physical invention have been developed and tested successfully in laboratory settings using human hair swatches as the testing medium.

36 combinations of both a host or donor product and the chemical formulation of the invention have been presented to an independent FDA certified testing laboratory for HPLC testing. The intent was to expose the levels of toxic dye intermediates found in this unique combination of hair coloring products. The FDA bar was set at 5% and our testing has shown the highest testing result of 3.2%. The HPLC testing has confirmed that the additive disclosed herein falls within a defined safety limit set by the FDA for hair coloring products.

The invention has been tested successfully on over 500 human test subjects with minimal allergic reactions occurring.

Formulation Reference Material

A key element of the educational/instructional component is the disclosure of the example "Permanent Hair Color Formulation Table" chart 10 in FIG. 1. We refer to this component as the "Permanent Hair Color Formulation Table" or the chart 10. This chart 10 is a major breakthrough in the hair-coloring industry because accurate instructions in the application of permanent hair colors have been missing or relevant to only a single hair color line. The Permanent Hair Color Formulation Table (chart 10) is considered a universal tool that can be used with most product brands. The Permanent Hair Color Formulation Table (chart 10) is an example and can be redrafted for each donor product type and/or brand.

The concept behind the Permanent Hair Color Formulation Table (chart 10) is to gather and record information about a client's hair coloring process so that a specific hair color formulation may be produced. One of the greatest challenges that hairdressers face is mixing the correct hair coloring formulation to use on a client and this table takes the guesswork out of the process. The chart 10 is designed to produce a 30 gram hair coloring solution by salvaging active and carrier ingredients from other permanent hair color solutions and combining them with the disclosed additive. In some embodiments, an alkali abundant solution is used because an alkali is present within the salvaged permanent hair color solution.

The Permanent Hair Color Formulation Table (chart 10) works as an 8-step process whereas a hairdresser enters data into the table by populating specific boxes that, when calculated, produce a formula (sum). This eight-step process is better understood by visually aligning the text explanation with the actual chart. The chart 10 is presented as a drawing in FIG. 1.

Chemical Formulation

The term "chemical formulation" is to be defined as a chemical formula, mixture or blend of chemicals developed to perform a defined purpose within the hair coloring process and considered the basis of this invention. The chemical formulation is furthermore divided into multiple segments based on the intent of the specific ingredient's performance.

The physical form of the chemical formulation may take that of a solid, powder, liquid or any combination of these physical forms.

A "hair coloring" segment of the formula comprises pure hair coloring dyes in their rawest form. These dyes can include oxidation dyes and may also be blended with basic dyes, direct dyes or cationic dyes. In addition, this family of hair dyes includes any future or past dyes that have or will effectively color hair.

A "carrier/delivery" segment of the formulation comprises a group of ingredients that's specific purpose is to deliver hair dyes in a precise manner. These ingredients are generally chemically neutral and may alter the physical consistency of the formula to increase speed of flow and delivery.

A "reactive" segment of the formula comprises a group of chemicals designed to create an active chemical reaction. These ingredients may breakdown and alter the host product, adjust pH or modify and enhance the newly applied hair dyes.

The chemical formulation can perform some or all of the following tasks:

(a) Maintain a low oxygen content in the formula so that the formula remains stable and uncontaminated.

(b) Act as a carrier or delivery formulation in which to deliver precise amounts of hair dyes in a measurable form.

(c) Control the speed, flow and accuracy of hair dye delivery.

(d) Manage the pH level to control and manipulate the hair cuticle's mechanical functions.

(e) Salvage or mask ingredients from other host hair coloring products.

(f) Clean, encapsulate or contain toxic residues left behind during the hair coloring process.

Process of Use

Using the invention begins with selecting a donor or host product. There are many hair coloring products or formulas available and they range from temporary to permanent. The primary objective in establishing a starting point is determining what the hairdresser or colorists is trying to achieve. These options range from maintaining a prior hair coloring service up to applying a permanent hair color service on a new client with uncolored hair.

Charting

The second step in using the invention correctly is gathering data about the client's past history as relevant to the hair-coloring process. Questions included can include: When did you color your hair last?, What products have you used before?, Have you shown any allergic reactions to hair coloring solutions before?. The charting step can include a list of questions related to the condition of the hair such as: What color it is now?, How much grey is present?, What is the physical condition of the hair? The charting step can also include questions about what the client is seeking to achieve through the hair coloring service, such as: What color do they want to be?, How long do they want their hair to be?, When do they plan on changing the their color again? The data gathered about the client's past history, allergies and hair condition are relevant to resetting the correct donor product for use with the disclosed additive and/or for determining whether the hair must be pre-treated to correct damage before a hair coloring process is applied.

The answers to all the questions can be applied to a formulation table, chart 10 or a software program. This charting process is part of the disclosure as no other similar charting process currently exists. All possible answer combinations are aligned with our complete physical product line of capsules, tablets, sachets or vials thus resulting in a sum that equals and aligns with a specific product or combination of more than one.

Once the correct physical product of the invention is selected, it becomes time to mix and blend the correct ingredients to create an active hair coloring solution. The charting process is extensive and because of this we will revisit this area later and share some actual sample charts for viewing.

Mixing

The formulating process begins by selecting each part of the formula and having these ingredients ready for mixing. A typical ingredient list will include three parts but in some cases more. It is critical that each ingredient be measured precisely by using a scale, balance or measuring cup.

1. Donor or Host Product
2. Capsule, Tablet, Vial or Sachet*
3. An Oxidizer

In all cases we will establish a basis for the formula by determining an amount of hair coloring solution to make. This amount will align with the application requirements in order to insure that enough of the solution is made to complete the hair coloring process. In most cases, a 30 g base will provide enough to complete the application requirements and the disclosure has been aligned for a 30 g base. This 30 g base can be duplicated many times, if needed, but it is always a good idea to mix fresh ingredients more often than letting older mixtures sit.

The 30 g base will be established by measuring 30 g of the host or donor product and placing it in a mixing bowl. Second is the process of adding the physical chemical formula of the invention by either opening a capsule or sachet and pouring the contents into the same mixing bowl. And third, adding a specified amount and proper level of liquid oxidizer such as hydrogen peroxide to the same bowl. All ingredients are thoroughly blended until all ingredients are dissolved and uniformly blended thus beginning the catalyst process of activating the ingredients.

It is important to note that future embodiments of the invention may alter this mixing or blending process by simplifying it for the hairdresser. Our selected package may hold a reservoir or void to accept the oxidizer so that it can be inserted into the package and blended as a separate step. This process is best understood by observing a favorable condition in which this process can take place.

An example is filling a glass vial with a precise amount of the chemical formulation of the invention that only fills one quarter of the total volume capacity and leaving three quarters filled with an inert gas. Once the vial is opened the inert gas dissipates and the void is now filled by the hairdresser with an oxidizer. The oxidizer can be filled to a predetermined line, the vial cap can be reattached and the vial can be shaken to blend both the chemical ingredients and oxidizer. Once blended these ingredients can be added to the host or donor product as a single alternative step.

Any single delivery form of the physical invention chemical formulation

Application

It is usually wise to map out a hair coloring service and segment the hair into work zones before mixing the hair coloring solution. In most cases, there are different conditions on a client's scalp. A typical condition will involve newly grown hair at the root line followed by some hair that has previously been colored and followed again by some hair that may be damaged physically at the ends. In many cases a different 30 g hair color formula will need to be mixed to tackle each of these problem areas independently.

Once all the ingredients are blended and activated, they are applied to the proper segmented area of hair on the scalp using a typical applicator brush or wand. In some cases, foils are used to isolate certain strands of hair to provide for a more precise variegated outcome.

After application on the hair, the coloring solution will be allowed to process chemically. This action will transform the hair shaft through multiple phases of processing thus resulting in reaching its final desired effect. The applicator usually views the final phase of this process carefully to determine when it is finished.

The hair is then washed with water to stop the chemical reaction and continual coloring of the hair shaft. Various processing aids can optionally be used, such as hair dryers, steamers and caps to increase the temperature to excel the processing speed of the solution.

What has been described is a hair coloring additive and method of use that provides highly accurate and long-lasting hair coloring effects. In this disclosure, there are shown and described only the preferred embodiments of the invention, but, as aforementioned, it is to be understood that the invention is capable of use in various other combinations and environments and is capable of changes or modifications within the scope of the inventive concept as expressed herein.

What is claimed is:

1. A hair coloring composition, comprising:
an additive comprising:
  a chemical formulation comprising:
    a plurality of raw oxidation dye molecules and an excipient; and
  a donor hair product as a temporary, semi-permanent, demi-permanent and/or permanent hair color product comprising:
    at least one of a surfactant, a carrier solution or water;
    at least one of an alkali, an antioxidant, a reducing agent or a solvent; and
    at least one of oxidation dyes, basic dyes, direct dyes or cationic dyes;
  and the additive and donor hair product each comprising an independent source of hair dye to create a mixture comprising hair dye sourced from each the additive and the donor hair product; and wherein the raw oxidation dye molecules of the additive comprise a size of less than 6.2 angstrom when added to the hair coloring composition.

2. The hair coloring composition of claim 1, wherein, the raw oxidation dye molecules comprise one of a coupler, a precursor and a mixture of a coupler and a precursor.

3. The hair coloring composition of claim 1, wherein the additive is chemically neutral.

4. The hair coloring composition of claim 1, wherein the additive is configured to control one of a speed, delivery and a speed and delivery of all molecules and chemicals comprising the mixture.

5. The hair coloring composition of claim 4, wherein the additive is configured to do one of blocking, metering or screening unwanted chemical components of the donor hair product from entering the cuticle or cortex of a hair shaft.

6. The hair coloring composition of claim 4, wherein the additive controls the speed and a delivery rate of dye molecules within the mixture based on their physical size to form a single color tone within the hair shaft cortex.

7. The hair coloring composition of claim 4, wherein the additive is configured to encapsulate at least one unwanted chemical component of the donor hair product from being active in the mixture.

8. The hair coloring composition of claim 4, wherein the additive is configured to dismantle at least one unwanted chemical component of the donor hair product, salvage at least one usable part of the unwanted chemical component, and discard at least one unusable part of the unwanted chemical component.

9. The hair coloring composition of claim 2, wherein the excipient comprises a carrier ingredient, wherein the carrier ingredient comprises a glidant with chemically neutral characteristics and is configured to increase one of a speed of flow or chemical delivery rate of all ingredients within the additive, thus making the additive the dominant component of the mixture.

10. The hair coloring composition of claim 2, wherein the additive further comprises a reducing agent.

11. The hair coloring composition of claim 10, wherein the excipient further comprises a binder.

12. The hair coloring composition of claim 11, wherein the additive is packaged separately in a single dose that aligns with one or more donor hair products, and wherein the additive further comprises a packaging in an environmentally secure atmosphere containing a single dose.

13. The hair coloring composition of claim 12, wherein the additive comprises one of a solid, powder, liquid and a combination of a solid, powder and liquid.

14. A method of coloring hair comprising the steps of:
Mixing or blending at least two chemical formulations:
a first chemical formulation is an additive comprising a raw oxidative dye molecules and a carrier solution comprising an excipient;
a second chemical formulation is a donor hair product comprising at least one or more of a temporary hair color, semi-permanent hair color, demi-permanent hair color, permanent hair color or bleaching hair color;
applying the mixture of the chemical formulations to hair and allowing the raw oxidation dye molecules of the additive to pass through the cuticle and into one of cortex and medulla of the hair shift;
enlarging the raw oxidation dye molecules located in one of the medulla and cortex by oxidizing them within the medulla and cortex, causing them to grow in a larger size;
stopping the hair coloring process and closing the cuticle of the hair shift; and
trapping the raw oxidation dye molecules in the medulla and cortex.

15. The method of claim 14, wherein the raw oxidation molecules comprise one of a coupler, precursor and both a coupler and precursor.

16. The method of claim 14, wherein the chemical formulation is configured to control one of a speed delivery and the speed and delivery of all molecules and chemicals comprising the solution.

17. The method of claim 14, wherein the chemical formulation is configured to do one of blocking, metering or screening unwanted chemical components of the donor hair product from entering one of the chemical formulation, cuticle and cortex.

18. The method of claim 14, wherein the chemical formulation is configured to control the speed and flow rate of all dye molecules based on their physical size.

19. A method of coloring hair comprising the steps of:
selecting one or more of a donor hair coloring product comprising temporary hair color, semi-permanent hair color, demi-permanent hair color, permanent hair color or bleaching hair color;
determining a client's existing hair color level and condition;
using a predetermining chart to determine the available new colors to client;
using the predetermining chart to determine the amount of an additive to mix with the donor hair coloring product; and
mixing 30 grams of the donor hair coloring product and the additive and;
applying the donor hair coloring product and the additive mixture to the client's hair, wherein the additive comprises a raw oxidative molecules and a carrier solution comprising an excipient.

20. The method of claim 19, wherein the predetermined chart further comprises an electronic computer implemented software-based chart configured to gather and calculate hair coloring data, wherein hair coloring data comprises the client's existing hair color level, amount of grey hair, physical condition and final tonal expectations.

* * * * *